US010166036B2

(12) United States Patent
Hanna et al.

(10) Patent No.: US 10,166,036 B2
(45) Date of Patent: Jan. 1, 2019

(54) VARIABLE SUCTION CONTROL

(71) Applicant: Gyrus ACMI, Inc., Southborough, MA (US)

(72) Inventors: Stephen M. Hanna, Norwalk, OH (US); Tim E. Mackey, Marble Head, OH (US); Mark C. Morris, Toledo, OH (US)

(73) Assignee: Gyrus ACMI, Inc., Southborough, MA (US)

( * ) Notice: Subject to any disclaimer, the term of this patent is extended or adjusted under 35 U.S.C. 154(b) by 94 days.

(21) Appl. No.: 14/865,253

(22) Filed: Sep. 25, 2015

(65) Prior Publication Data
US 2016/0106450 A1  Apr. 21, 2016

Related U.S. Application Data

(60) Provisional application No. 62/064,555, filed on Oct. 16, 2014.

(51) Int. Cl.
*A61B 17/225* (2006.01)
*A61M 1/00* (2006.01)
*A61B 17/22* (2006.01)

(52) U.S. Cl.
CPC ......... *A61B 17/225* (2013.01); *A61M 1/0035* (2014.02); *A61M 1/0041* (2013.01); *A61B 2017/22079* (2013.01)

(58) Field of Classification Search
CPC .............. A61M 1/0047; A61M 1/0033; A61M 1/0039; A61M 1/0041; A61M 1/0043; A61M 1/0064; F16K 5/0414; A61B 17/225

USPC .......................................... 251/208, 209, 310
See application file for complete search history.

(56) References Cited

U.S. PATENT DOCUMENTS

| | | | | |
|---|---|---|---|---|
| 1,313,105 A | * | 8/1919 | Moran | F16K 11/087 137/625.41 |
| 3,395,705 A | * | 8/1968 | Hamilton | A61M 1/0047 604/119 |
| 4,595,127 A | | 6/1986 | Stoody | 222/135 |
| 4,925,450 A | * | 5/1990 | Imonti | A61M 1/0043 604/240 |
| 5,492,527 A | | 2/1996 | Glowa et al. | 604/22 |

(Continued)

FOREIGN PATENT DOCUMENTS

WO  WO-2014/021965 A2  2/2014

*Primary Examiner* — Andrew Gilbert
*Assistant Examiner* — John Doubrava
(74) *Attorney, Agent, or Firm* — Harrington & Smith

(57) ABSTRACT

An apparatus including a housing, an electrical conductor, and a suction control valve. The housing forms a handle and a shaft. The housing defines a suction channel from a distal end of the shaft. The electrical conductor extends to the distal end of the shaft. The suction control valve is connected to the suction channel at the handle. The suction control valve includes a valve body having a first channel and a second channel connected to the first channel, where the first channel forms a portion of the suction channel; and a valve barrel rotatably connected to the valve body. The valve barrel includes a rotatable ring extending around the handle and forming a portion of the housing. The ring includes an orifice configured to be rotated into and out of registration with an end of the second channel as the ring is rotated about the valve body.

18 Claims, 5 Drawing Sheets

(56) References Cited

U.S. PATENT DOCUMENTS

| | | | |
|---|---|---|---|
| 5,830,214 A * | 11/1998 | Flom | A61B 18/1482 |
| | | | 606/41 |
| 6,129,701 A * | 10/2000 | Cimino | A61M 1/0047 |
| | | | 604/30 |
| 6,193,672 B1 | 2/2001 | Clement et al. | |
| 6,436,067 B1 | 8/2002 | Deng et al. | 604/32 |
| 7,682,333 B2 * | 3/2010 | Deng | A61B 17/32002 |
| | | | 604/35 |
| 2014/0060577 A1 * | 3/2014 | Bruders | A47L 11/4044 |
| | | | 134/6 |

* cited by examiner

VARIABLE SUCTION CONTROL

CROSS REFERENCE TO RELATED APPLICATION

This application claims priority on U.S. provisional patent application No. 62/064,555 filed Oct. 16, 2014 which is hereby incorporated by reference in its entirety.

BACKGROUND

Technical Field

The exemplary and non-limiting embodiments relate generally to a medical instrument and, more particularly, to a medical instrument having a suction control.

Brief Description of Prior Developments

Some medical instruments, such as a lithotripter for example, provide suction to remove fluids and debris from inside a patient.

SUMMARY

The following summary is merely intended to be exemplary. The summary is not intended to limit the scope of the claims.

In accordance with one aspect, an example embodiment is provided in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle. The suction control valve comprises a valve body having a first channel and a second channel connected to the first channel, where the first channel forms a portion of the suction channel; and a valve barrel rotatably connected to the valve body, where the valve barrel comprises a rotatable ring extending around the handle and forming a portion of the housing, and wherein the ring comprises an orifice configured to be rotated into and out of registration with an end of the second channel as the ring is rotated about the valve body.

In accordance with another aspect, an example embodiment is provided in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle. The suction control valve comprises an air inlet control value comprising a ring rotatably connected to the handle about a center axis of rotation which is aligned with a longitudinal axis of the handle.

In accordance with another aspect, an example embodiment is provided in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle. The suction control valve comprises an air inlet valve member rotatably connected to the handle, where the air inlet valve member comprises an air metering orifice, where the air inlet valve member is configured to rotate the air metering orifice relative to an entrance into an air inlet hole connected to the suction channel to vary suction in the suction channel in the shaft, and where the air metering orifice and/or the entrance to the air inlet hole comprises a non-circular cross section.

In accordance with another aspect, an example method comprises providing a housing of an apparatus with a handle and a shaft, where the shaft extends from the handle, where the housing defines a suction channel from a distal end of the shaft and through the handle; providing an electrical conductor through the handle and to the distal end of the shaft; and connecting a valve barrel to a valve body in the handle, where the valve barrel comprises a rotatable ring extending around the handle and forming a portion of the housing, and wherein the ring comprises an aperture configured to be rotated into and out of registration with an air inlet orifice of the valve body as the ring is rotated about the valve body.

In accordance with another aspect, an example method comprises providing suction in a suction channel extending through a handle and shaft of a medical instrument; and rotating a ring on the handle to vary the suction in the shaft of the medical instrument, where the ring comprises an air metering orifice, where the ring is configured to rotate the air metering orifice relative to an entrance into an air inlet hole connected to the suction channel at the handle to vary suction in the suction channel in the shaft, and where the air metering orifice and/or the entrance to the air inlet hole comprises a non-circular cross section.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
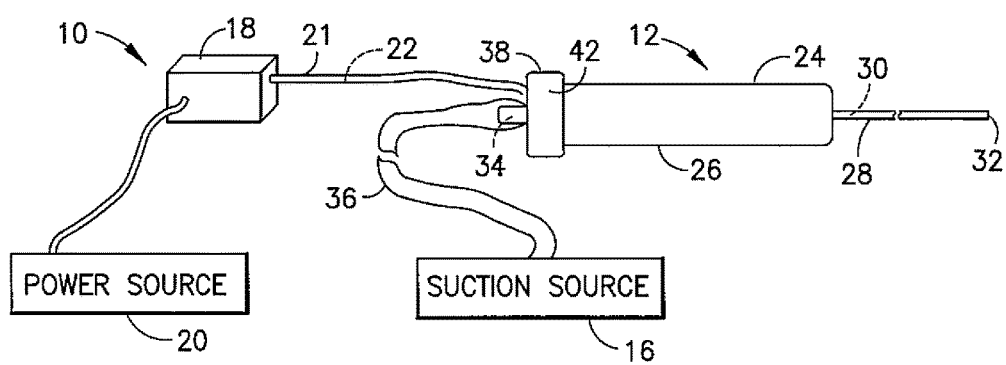
FIG. 1 is a diagram illustrating an example powered surgical instrument system.

Referring to FIG. 1, there is shown a schematic diagram of a powered surgical instrument system 10 incorporating features of an example embodiment. Although the features will be described with reference to the example embodiments shown in the drawings, it should be understood that features can be embodied in many alternate forms of embodiments. In addition, any suitable size, shape or type of elements or materials could be used.

The powered surgical instrument system 10 includes an apparatus 12, a vacuum or suction source 16, a control unit 18, and a power source 20 such as from a wall outlet for example. The suction source 16 may be an external suction source such as provided by attachment to a facility suction outlet provided on a wall. An electrical cable 21, having an electrical conductor 22 therein, extends from the control unit 18 into the apparatus 12.

Figure 2:
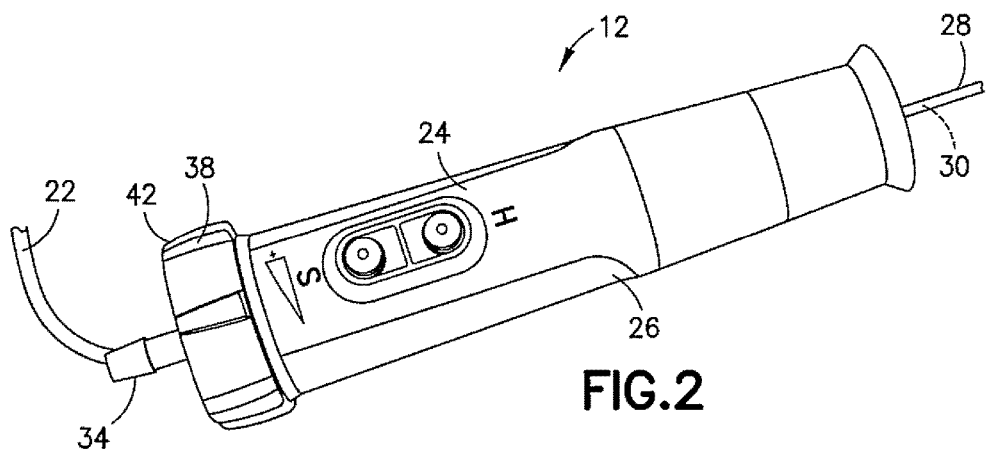
FIG. 2 is a partial side view of the apparatus shown in FIG. 1.

In this example embodiment the apparatus 12 is a lithotriptor (a device used to crush or fragment a calculus in lithotripsy). However, features as described herein may be used in other types of medical instruments. Referring also to FIG. 2, the apparatus 12 generally comprises a housing 24 which at least partially forms a handle 26 and a shaft 28. The shaft 28 extends from the handle 26 in a general cantilever fashion. The apparatus 12 has a suction channel 30 which extends through the handle 26 and to the distal end 32 of the shaft 28. A rear end 34 of the suction channel 30 is configured to have a suction tube 36 connected thereto. The suction tube 36 connects the suction channel 30 to the suction source 16. The electrical conductor 22 also extends through the handle 24 and shaft towards the distal end 32. A liquid and/or gas fluid source (not shown) may be connected to an endoscope or access sheath (not shown) used by the user/physician during a procedure to provide fluid proximate a location of the distal end 32 of the apparatus 12.

Figure 3:
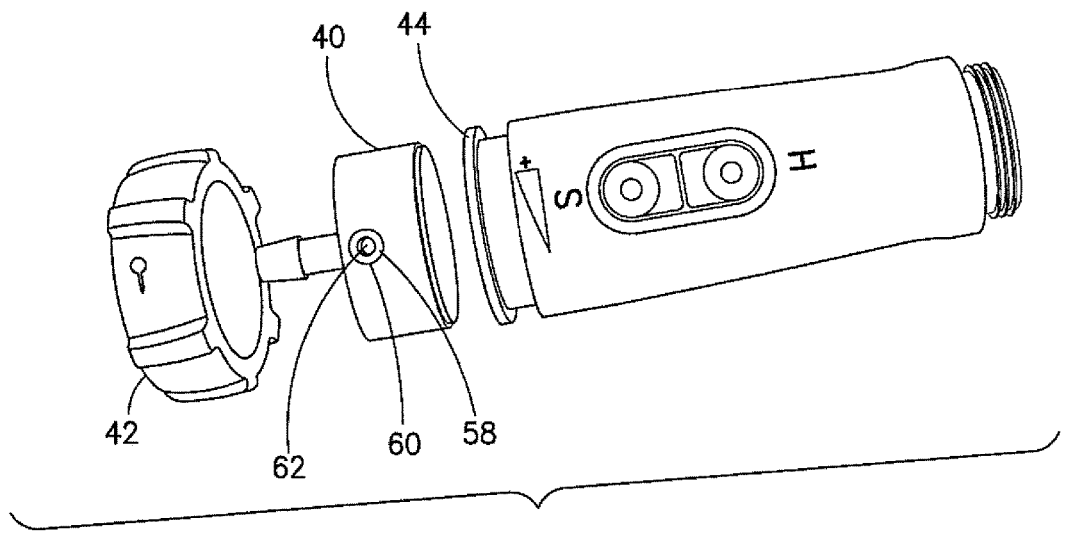
FIG. 3 is an exploded view of some of the components of the apparatus shown in FIG. 2.

The apparatus 12 includes an adjustable suction control valve or air inlet valve 38. Referring also to FIG. 3, an exploded perspective view of some of the components of the valve 38 are shown. The valve 38 generally comprises a valve body 40 and a valve barrel or actuator 42. The valve body 40 is attached, fixedly and stationarily, by fasteners (not shown) to a member 44 of the housing 24. The valve barrel 42 is rotatably connected to the valve body 40. In an alternate example embodiment the valve could comprise a valve stem as the valve actuator which projects into the valve body.

Figure 4:
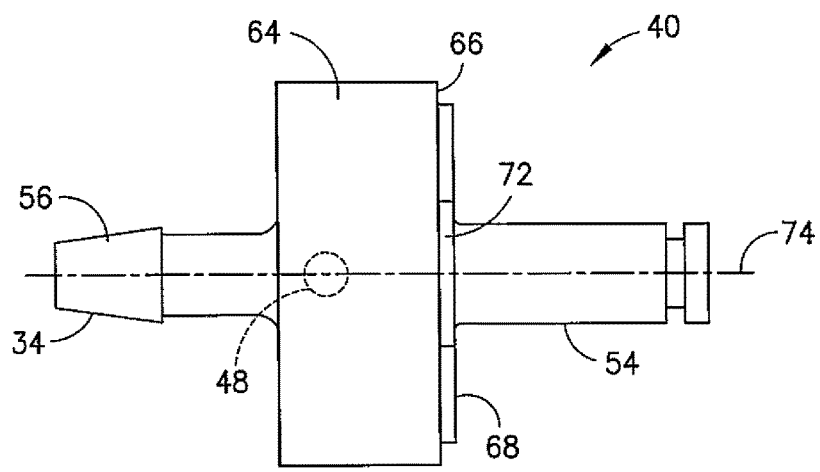
FIG. 4 is a side view of the valve body shown in FIG. 3.
Figure 5:
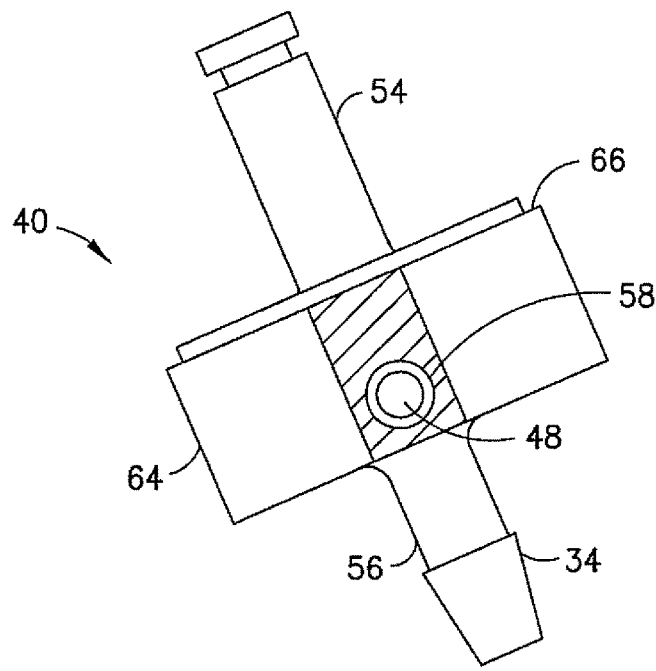
FIG. 5 is a side view of the valve body shown in FIG. 3 with a partial cut away section.
Figure 6:
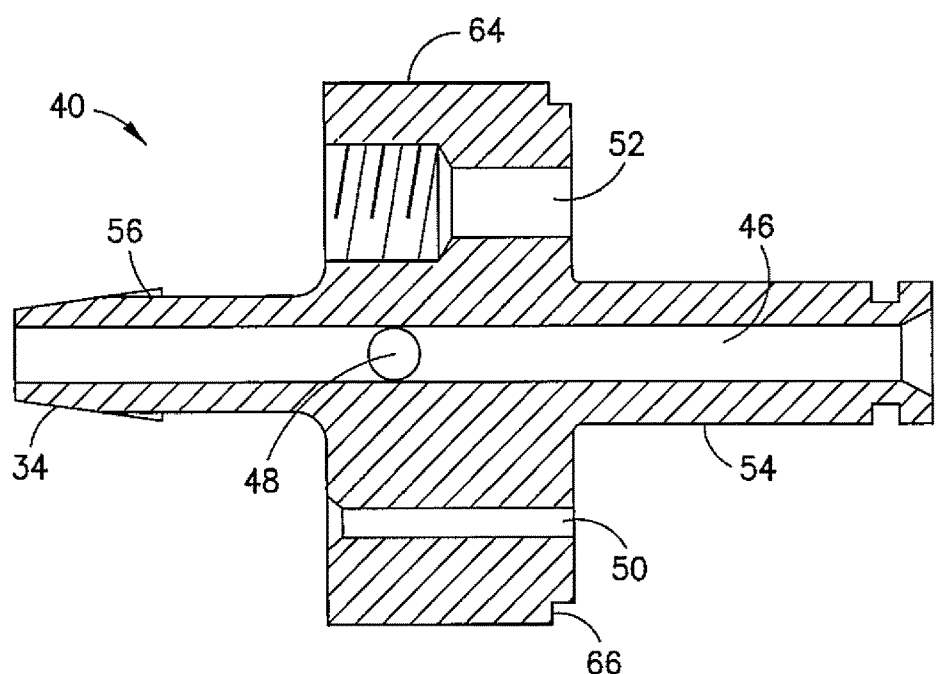
FIG. 6 is a cross sectional view of the valve body shown in FIGS. 4-5.

Referring also to FIGS. 4-6, the valve body 40 is a one piece member comprising a first channel 46, a second channel 48, fastener holes 50, an electrical conductor hole 52, a front projection 54 and a rear projection 56. The first channel 46 forms part of the suction channel 30. The first channel 46 extends through the front and rear projections 54, 56. The rear projection 56 forms the rear end 34 of the suction channel 30. The second channel 48 intersects the first channel 46, and extends to a lateral side of the valve body 40. This example embodiment shows the valve body with only one second channel 48. However, in an alternate example two or more second channels 48 could be provided, such as located at different radial angles about the center longitudinal axis of the valve body for example. A recessed seat 58 is located at an entrance to the second channel 48 which has a seal 60 therein (see FIG. 3). The seal 60 has a hole 62 therethrough.

The valve body 40 has a main section 64 which has a ledge 66 at a front end 68. The ledge 66 is sized and shaped to receive an inwardly extending rim 70 (see FIG. 8) of the valve barrel 42. The front end 68 also includes a recess 72 extending radially inwardly from the ledge 66. In this embodiment the recess 72 has an angle relative to the longitudinal centerline 74 of the valve body 40 of about 45 degrees. However, in alternate embodiments the angle might be more or less than 45 degrees. For example, the angle could be about 60 degrees.

Figure 7:
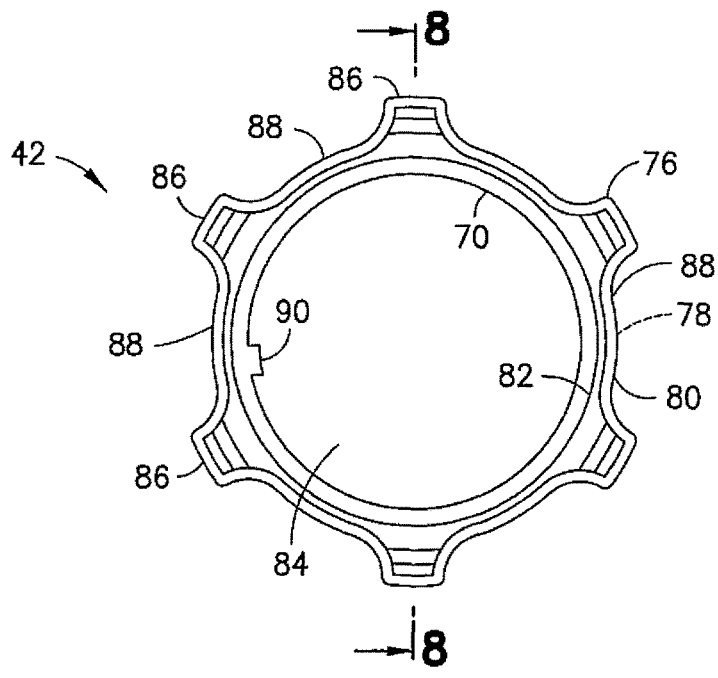
FIG. 7 is an end view of the valve barrel shown in FIGS. 1-3.
Figure 8:
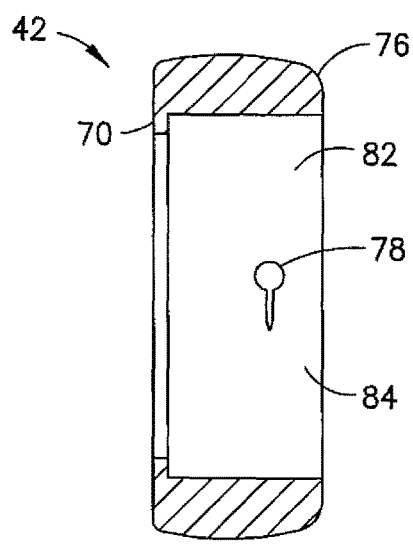
FIG. 8 is a cross sectional view of the valve barrel shown in FIG. 7 taken along line 8-8.
Figure 9:
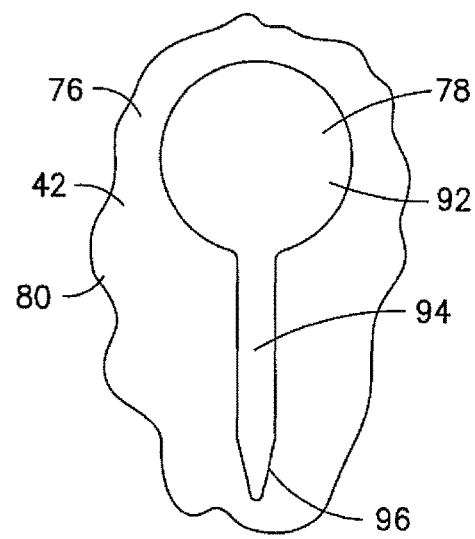
FIG. 9 is an enlarged view of the orifice in the valve barrel shown in FIG. 8.
Figure 10A:
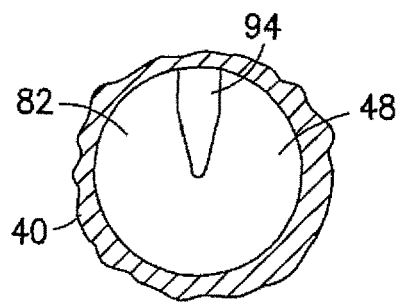
FIGS. 10A-10D are views illustrating intermediate partially open valve positions with different size apertures created based upon position of the valve barrel relative to the valve body.
Figure 10B:
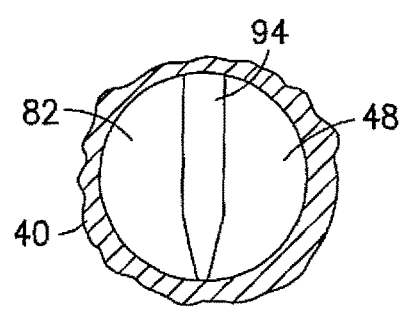
Figure 10C:
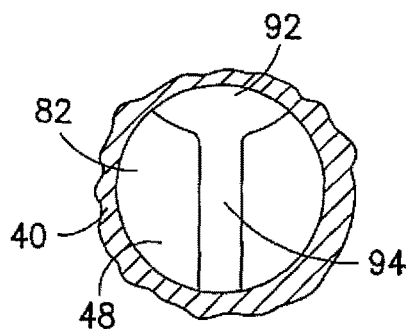
Figure 10D:
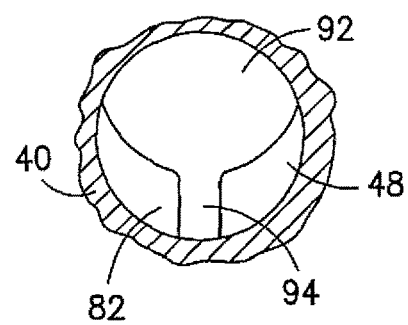

Referring also to FIGS. 7-9, the valve barrel 42 generally comprises a ring or ring shaped member 76. The ring 76 has an orifice 78 therethrough between an outer lateral side 80 and an inner side 82 at a center aperture 84 of the ring 76. The ring 76 has a single orifice 78 in this example. However, in an alternate example the ring could comprise two or more orifices, such as located at different radial angles about the centerline of the aperture 84. In this example the outer lateral side 80 comprises projections or ridges 86, and recessed areas 88 between the projections 86. The entrance into the orifice 78 is located at one of the recessed areas 88 between two of the projections 86. The projections 86 provide raised areas for a user's thumb to contact. The projections or ridges 86 make rotating the valve barrel 42 about the valve body 40 easier for the user without the user's thumb slipping off the ring 76.

The rim 70 of the valve barrel 42 is located at the ledge 66 of the valve body 40. The rim 70 is rotatably captured between the valve body 40 and the member 44. Thus, when the valve body 40 is stationarily attached to the member 44 by fasteners, the valve barrel 42 is fixedly, but rotatably attached around the valve body 40. The inner side 82 of the ring 76, in addition to the rim 70, includes an inwardly extending projection 90. The projection 90 is located in the recess 72 of the valve body 40. The projection 90 is smaller than the recess 72 such that the valve barrel 42 is rotatable about the valve body 40. The projection 90 is able to contact opposite sides of the recess 72 to limit axial rotation of the valve barrel about the valve body. Thus, the projection 90 and the recess 72 function as a rotational limiter to limit axial rotation of the valve barrel 42 about the valve body 40 to a predetermined angle of rotation, such as an angle of between 30-90 degrees for example.

Referring particularly to FIG. 9, the orifice 78 in this example has an entrance with a generally non-circular cross sectional shape. The shape, in this example, comprises a first section 92 with a general circular cross section and a second section 94 with a general non-circular cross section. In this example the second section 94 has a general slot shape with a tapered end 96. In alternate example embodiments, more or less than two sections may be provided, and different shapes other than those shown in this example may be provided.

The orifice 78 forms an air inlet hole for the entrance into the second channel 48. In combination with the positioning of the valve barrel 42 relative to the entrance into the second channel 48 of the valve body 40, the shape of the orifice 78 is used to vary suction in the suction channel 46; particularly at the entrance into the suction channel at the distal end 32 of the shaft 28.

The valve barrel 42 is rotatable on the valve body 40 between a first fully closed position of the valve and a second fully open position of the valve. The fully closed position comprises the valve barrel 42 completely covering the entrance to the second channel 48 with no portion of the orifice 78 registered with the entrance to the second channel 48. Thus, atmospheric air is prevented from entering the entrance to the second channel 48 through the valve barrel 42. The seal 60 seals the entrance to the second channel 48 with the ring 76.

The fully open position of the valve comprises the first section 92 of the orifice 78 being aligned with the entrance to the second channel 48 such that the ring 76 does not substantially block air from entering the second channel 48. The cross sectional size and shape of the first section 92 of the orifice 78 is about the same cross sectional size and shape as the second channel 48. Air flowing into the suction channel 30 from the valve 38 reduces the suction at the entrance to the suction channel 30 at the distal end 32 of the shaft 28.

The valve 38, in this example embodiment, has a plurality of intermediate partially open positions between the fully closed position and the fully open position. Referring also to FIGS. 10A-10D, examples of some of the intermediate partially open positions are shown. Based upon the position of the valve barrel relative to the valve body, the aperture through the orifice and the entrance to the second channel 48 changes to vary the amount of air which can enter the second channel 48 through the valve barrel. For example, the size of the aperture increases through the examples of FIGS. 10A through 10D.

The valve 38 may be used to provide a suction control design which uses ingression of air through the side of the handle in order to reduce the vacuum or suction pressure. The suction control ring has an orifice geometry that restricts air flow, therefore, allowing the suction flow to be throttled and not simply set to ON or OFF. The functional use of features as described herein is to allow a physician to meter the suction during a procedure, and not simply have suction either ON or OFF.

Figure 11:
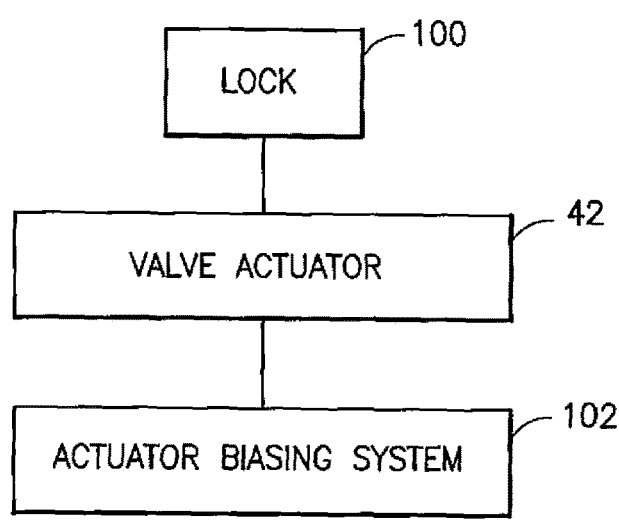
FIG. 11 is a diagram illustrating features of an alternate example embodiment.

Referring also to FIG. 11, an example embodiment of the apparatus may comprise a lock 100 and a biasing system 102 connected to the actuator 42 of the valve 38. The lock 100 may be configured to lock the position of the actuator 42 relative to the valve body 40. The lock 100 may be a user actuated lock for example. The lock 100 may be configured to help prevent the position of the valve 38 from inadvertently changing. The biasing system 102 may comprise a spring, for example, which is adapted to bias the actuator 42 at a predetermined position relative to the valve body 40. For example, the spring could bias the actuator 42 at a position on the handle 26 for the valve 38 to have a fully open position. In one type of example embodiment the valve 38 would be biased by the biasing system 102 to the fully open position, but the user could manually move the actuator 42 to a fully closed or partially closed position, and then lock the actuator 42 at that position by means of the lock 100. The biasing system may maintain the air metering orifice in an open position and the locking member may be used to hold the position of the valve actuator at a ,desired rotation. In alternate example embodiments the lock 100 and/or the biasing system 102 might not be provided.

An example embodiment may be provide in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle. the suction control valve comprises a valve body having a first channel and a second channel connected to the first channel, where the first channel forms a portion of the suction channel; and a valve barrel rotatably connected to the valve body, where the valve barrel comprises a rotatable ring extending around the handle and forming a portion of the housing, and wherein the ring comprises an orifice configured to be rotated into and out of registration with an end of the second channel as the ring is rotated about the valve body.

The orifice may comprise a non-circular cross section. The orifice may comprise a first section with a general circular cross section and a second section with general non-circular cross section. The ring may be rotatably connected to the handle about a center axis of rotation which is aligned with a longitudinal axis of the handle. The ring may comprise ridges extending from an exterior side of the ring, and where the orifice is located between two of the ridges.

The valve body may comprise a projection extending out of a rear end of the handle, where the first channel extends through the projection, and where the projection is configured to have a suction tube mounted thereon. The valve body may comprise a through hole having the electrical conductor extend therethrough. The ring may be located around a rear end of the handle. The suction control valve may comprise a fully open position, a fully closed position, and at least one partially open position. The at least one partially open position may comprise multiple partially open positions to allow a user to variably adjust an amount of air entering the suction channel and thereby vary the suction at the distal end of the shaft. The valve barrel may be configured to be moved by a thumb of a hand of a user as the user is grasping the housing at the handle with the hand.

An example embodiment may be provide in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle, where the suction control valve comprises an air inlet control value comprising a ring rotatably connected to the handle about a center axis of rotation which is aligned with a longitudinal axis of the handle.

An example embodiment may be provide in an apparatus comprising a housing forming a handle and a shaft, where the shaft extends from the handle, where the housing defines a suction channel from a distal end of the shaft and through the handle; an electrical conductor extending from the handle through the shaft to the distal end of the shaft; and a suction control valve connected to the suction channel at the handle, where the suction control valve comprises an air inlet valve member rotatably connected to the handle, where the air inlet valve member comprises an air metering orifice, where the air inlet valve member is configured to rotate the air metering orifice relative to an entrance into an air inlet hole connected to the suction channel to vary suction in the suction channel in the shaft, and where the air metering orifice and/or the entrance to the air inlet hole comprises a non-circular cross section.

An example method may comprise providing a housing of an apparatus with a handle and a shaft, where the shaft extends from the handle, where the housing defines a suction channel from a distal end of the shaft and through the handle; providing an electrical conductor through the handle and to the distal end of the shaft; and connecting a valve barrel to a valve body in the handle, where the valve barrel comprises a rotatable ring extending around the handle and forming a portion of the housing, and wherein the ring comprises an aperture configured to be rotated into and out of registration with an air inlet orifice of the valve body as the ring is rotated about the valve body.

An example method may comprise providing suction in a suction channel extending through a handle and shaft of a medical instrument; and rotating a ring on the handle to vary the suction in the shaft of the medical instrument, where the ring comprises an air metering orifice, where the ring is configured to rotate the air metering orifice relative to an entrance into an air inlet hole connected to the suction channel at the handle to vary suction in the suction channel in the shaft, and where the air metering orifice and/or the entrance to the air inlet hole comprises a non-circular cross section.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An apparatus comprising:
a housing forming a handle and a shaft, the shaft extends from the handle, and the housing defines a suction channel from a distal end of the shaft and through the handle;
an electrical conductor extending from the handle through the shaft to the distal end of the shaft; and
a suction control valve connected to the suction channel at the handle, the suction control valve comprises:
a valve body having a first channel and a second channel connected to the first channel, the first channel forms a portion of the suction channel, the second channel having a recessed seat at an entrance to the second channel;
a valve barrel rotatably connected to the valve body, the valve barrel comprises a rotatable ring surrounding the valve body and forming a portion of the housing, the ring comprises an orifice configured to be rotated into and out of registration with an end of the second channel as the ring is rotated about the valve body; and
a seal configured to be aligned with the second channel at times the valve barrel is rotated to an open position and to a closed position, the seal comprising a first end and an opposite second end, the first end of the seal is received at the recessed seat, the seal comprising an opening extending from the first end of the seal to the opposite second end of the seal.

2. An apparatus as in claim 1 where the orifice has a non-circular cross section.

3. An apparatus as in claim 1 where the orifice has a first section with a general circular cross section and a second section with general non-circular cross section.

4. An apparatus as in claim 1 where the ring is rotatably connected to the handle about a center axis of rotation which is aligned with a longitudinal axis of the handle.

5. An apparatus as in claim 1 where the ring comprises ridges extending from an exterior side of the ring, and where the orifice is located between two of the ridges.

6. An apparatus as in claim 1 where the valve body comprises a projection extending out of a rear end of the handle, where the first channel extends through the projection, and where the projection is configured to have a suction tube mounted thereon.

7. An apparatus as in claim 1 where the valve body comprises a through hole having the electrical conductor extend therethrough.

8. An apparatus as in claim 1 where the ring is located around a rear end of the handle.

9. An apparatus as in claim 1 where the suction control valve comprises a fully open position, a fully closed position, and at least one partially open position.

10. An apparatus as in claim 9 where the at least one partially open position comprises multiple partially open positions to allow a user to variably adjust an amount of air entering the suction channel and thereby vary the suction at the distal end of the shaft.

11. An apparatus as in claim 1 where the valve barrel is configured to be moved by a thumb of a hand of a user as the user is grasping the housing at the handle with the hand.

12. An apparatus as in claim 1 further comprising a lock configured to lock the valve barrel at a predetermined position.

13. An apparatus as in claim 12 further comprising a biasing system configured to bias the valve barrel at a predetermined position.

14. An apparatus as in claim 1 wherein the seal is configured to prevent atmospheric air from entering the second channel by sealing the entrance to the second channel with the ring.

15. An apparatus comprising:
a housing forming a handle and a shaft, the shaft extends from the handle, and the housing defines a suction channel from a distal end of the shaft and through the handle;
an electrical conductor extending from the handle through the shaft to the distal end of the shaft; and
a suction control valve connected to the suction channel at the handle, the suction control valve comprises:
an air inlet control valve comprising a ring rotatably connected to the handle about a center axis of rotation which is aligned with a longitudinal axis of the handle, the ring comprising an orifice;
a second channel having a recessed seat at an entrance to the channel; and
a seal configured to be aligned with the second channel at times the ring is rotated to an open position and to a closed position, the seal comprising a first end and an opposite second end, the first end of the seal is received at the recessed seat, the seal comprising an opening extending from the first end of the seal to the opposite second end of the seal.

16. An apparatus comprising:
a housing forming a handle and a shaft, the shaft extends from the handle, and the housing defines a suction channel from a distal end of the shaft and through the handle;
an electrical conductor extending from the handle through the shaft to the distal end of the shaft; and
a suction control valve connected to the suction channel at the handle, the suction control valve comprises:
an air inlet valve member rotatably connected to the handle, the air inlet valve member comprises an air metering orifice, the air inlet valve member is configured to rotate the air metering orifice relative to an entrance into an air inlet hole connected to the suction channel to vary suction in the suction channel in the shaft, the air metering orifice and/or the entrance to the air inlet hole comprises a non-circular cross section, the entrance having a recessed seat; and
a seal configured to be aligned with the air inlet hole at times the air inlet valve member is rotated to an open position and to a closed position, the seal comprising a first end and an opposite second end, the first end of the seal is received at the recessed seat, the seal comprising an opening extending from the first end of the seal to the opposite second end of the seal.

17. A method comprising:
providing a housing of an apparatus with a handle and a shaft, the shaft extends from the handle, and the housing defines a suction channel from a distal end of the shaft and through the handle;

providing an electrical conductor through the handle and to the distal end of the shaft;

connecting a valve barrel to a valve body in the handle, the valve barrel comprises a rotatable ring extending around the handle and forming a portion of the housing, the ring comprises an aperture configured to be rotated into and out of registration with an air inlet orifice of the valve body as the ring is rotated about the valve body, the air inlet orifice having a recessed seat; and providing a seal configured to be aligned with the air inlet orifice of the valve body at times the valve barrel is rotated to an open position and to a closed position, the seal comprising a first end and an opposite second end, the first end of the seal is received at the recessed seat, the seal comprising an opening extending from the first end of the seal to the opposite second end of the seal.

18. A method comprising:

providing suction in a suction channel extending through a handle and shaft of a medical instrument;

rotating a ring on the handle to vary the suction in the shaft of the medical instrument, the ring comprises an air metering orifice, the ring is configured to rotate the air metering orifice relative to an entrance into an air inlet hole connected to the suction channel at the handle to vary suction in the suction channel in the shaft, the air metering orifice and/or the entrance to the air inlet hole comprises a non-circular cross section, the entrance into the air inlet hole having a recessed seat; and providing a seal configured to be aligned with the air inlet hole at times the ring is rotated to an open position and to a closed position, the seal comprising a first end and an opposite second end, the first end of the seal is received at the recessed seal, the seal comprising an opening extending from the first end of the seal to the opposite second end of the seal.

\* \* \* \* \*